(12) United States Patent
Naidu

(10) Patent No.: US 12,194,266 B2
(45) Date of Patent: Jan. 14, 2025

(54) EXTENSION SET TO REDUCE EXTENSION TUBE KINKING

(71) Applicant: Becton, Dickinson and Company, Franklin Lakes, NJ (US)

(72) Inventor: Jithendra Kumar Sathyanarayana Naidu, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 66 days.

(21) Appl. No.: 16/841,419

(22) Filed: Apr. 6, 2020

(65) Prior Publication Data

US 2020/0324100 A1    Oct. 15, 2020

Related U.S. Application Data

(60) Provisional application No. 62/831,525, filed on Apr. 9, 2019.

(51) Int. Cl.
*A61M 39/10*    (2006.01)
*A61M 25/00*    (2006.01)
(Continued)

(52) U.S. Cl.
CPC .......... *A61M 39/105* (2013.01); *A61M 25/02* (2013.01); *A61M 25/0606* (2013.01); *A61M 39/0247* (2013.01); *A61M 39/24* (2013.01); *A61M 2025/0059* (2013.01); *A61M 2025/0206* (2013.01); *A61M 2025/026* (2013.01);
(Continued)

(58) Field of Classification Search
CPC ................ A61M 39/105; A61M 25/02; A61M 25/0606; A61M 39/0247; A61M 39/24; A61M 2025/0059; A61M 2025/0206; A61M 2025/026; A61M 2025/028; A61M 2025/0293; A61M 2039/0258; A61M 2039/1077; A61M 2039/1083; A61M 2039/1088; A61M 5/1418; A61M 2025/0253; A61M 2025/024;
(Continued)

(56) References Cited

U.S. PATENT DOCUMENTS 3,630,195 A    12/1971    Santomieri
4,316,461 A    2/1982    Marais et al.
(Continued)

FOREIGN PATENT DOCUMENTS

AU    2010303425 A1    4/2012
AU    2016344417 A1    5/2018
(Continued)

*Primary Examiner* — Kevin C Sirmons
*Assistant Examiner* — Avery Smale
(74) *Attorney, Agent, or Firm* — Kirton McConkie; Whitney Blair; Kevin Stinger

(57) ABSTRACT

A vascular access system may include a catheter adapter and an extension set. The extension set may include a first end having a first connector coupled to the catheter adapter, a second end having a second connector, an extension tube disposed between the first end and the second end, and a brace configured to hold the extension tube in a curved position. The extension set may alternatively include a housing disposed between the first connector and the extension tube, where the housing is U-shaped or V-shaped and a fluid pathway extends through the housing.

12 Claims, 12 Drawing Sheets

(51) Int. Cl.
*A61M 25/02* (2006.01)
*A61M 25/06* (2006.01)
*A61M 39/02* (2006.01)
*A61M 39/24* (2006.01)

(52) U.S. Cl.
CPC ............ *A61M 2025/028* (2013.01); *A61M 2025/0293* (2013.01); *A61M 2039/0258* (2013.01); *A61M 2039/1077* (2013.01); *A61M 2039/1083* (2013.01); *A61M 2039/1088* (2013.01)

(58) Field of Classification Search
CPC .. A61M 2039/0261; A61M 2039/0264; A61M 39/10; A61M 39/12; A61M 2005/1586
See application file for complete search history.

(56) References Cited

U.S. PATENT DOCUMENTS

| | | | |
|---|---|---|---|
| 4,453,933 A | 6/1984 | Speaker | |
| 5,250,038 A * | 10/1993 | Melker | A61M 25/0032 604/167.01 |
| 5,456,671 A | 10/1995 | Bierman | |
| 5,702,371 A * | 12/1997 | Bierman | A61M 25/02 128/DIG. 26 |
| 5,947,931 A | 9/1999 | Bierman | |
| 2005/0234405 A1 | 10/2005 | Dikeman | |
| 2005/0256461 A1 | 11/2005 | Difiore | |
| 2005/0267445 A1* | 12/2005 | Mendels | A61M 39/10 604/534 |
| 2008/0147012 A1 | 6/2008 | Rome | |
| 2010/0168718 A1 | 7/2010 | Bellisario | |
| 2011/0313361 A1 | 12/2011 | Shipman | |
| 2012/0271239 A1 | 10/2012 | Andino et al. | |
| 2012/0271240 A1* | 10/2012 | Andino | A61M 25/02 604/180 |
| 2014/0128813 A1* | 5/2014 | Rosenhan | A61M 25/02 604/174 |
| 2014/0324014 A1* | 10/2014 | Lundgren | A61M 39/10 604/533 |
| 2014/0343531 A1 | 11/2014 | Larkin | |
| 2015/0250984 A1* | 9/2015 | Humphries | A61M 5/1418 29/428 |
| 2017/0120016 A1 | 5/2017 | Burkholz et al. | |
| 2017/0296788 A1 | 10/2017 | Andino et al. | |
| 2020/0030578 A1 | 1/2020 | Andino et al. | |
| 2020/0078564 A1 | 3/2020 | Blanchard et al. | |
| 2020/0101265 A1 | 4/2020 | Burkholz et al. | |
| 2020/0168718 A1 | 5/2020 | Iucolano et al. | |

FOREIGN PATENT DOCUMENTS

| | | |
|---|---|---|
| AU | 2019216675 A1 | 9/2019 |
| CA | 2107321 A1 | 4/1994 |
| CA | 2776239 A1 | 4/2011 |
| CA | 3001905 A1 | 5/2017 |
| CN | 104080508 A | 10/2014 |
| CN | 106620939 A | 5/2017 |
| CN | 206880907 U | 1/2018 |
| EP | 0593181 A2 | 4/1994 |
| EP | 3368129 A1 | 9/2018 |
| EP | 3669925 A1 | 6/2020 |
| ES | 2337529 T3 | 4/2010 |
| JP | H06190053 A | 7/1994 |
| JP | 2004041784 A | 2/2004 |
| JP | 2006026190 A | 2/2006 |
| JP | 2013507186 A | 3/2013 |
| JP | 2018532508 A | 11/2018 |
| JP | 2020006190 A | 1/2020 |
| SG | 11201802967X | 5/2018 |
| WO | 2011/044293 | 4/2011 |
| WO | 2011/060197 | 5/2011 |
| WO | 2017/074676 | 5/2017 |
| WO | 2020055587 A1 | 3/2020 |

* cited by examiner

EXTENSION SET TO REDUCE EXTENSION TUBE KINKING

RELATED APPLICATIONS

This application claims the benefit of U.S. Application No. 62/831,525, filed Apr. 9, 2019, and entitled EXTENSION SET TO REDUCE EXTENSION TUBE KINKING, which is incorporated herein in its entirety.

BACKGROUND

Infusion therapy, a common healthcare procedure, may be facilitated by a vascular access device. Hospitalized, home care, and other patients receive fluids, pharmaceuticals, and blood products via a vascular access device inserted into the vascular system. Blood withdrawal is another common healthcare procedure that may be facilitated by a vascular access device.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow angle through the skin into vasculature of the patient.

In order to verify proper placement of the introducer needle and/or the PIVC in the vein, a user generally confirms that there is "flashback" of blood in a flashback chamber of a PIVC assembly. Once placement of the needle has been confirmed, a user may temporarily occlude flow in the vein and remove the introducer needle, leaving the PIVC in place within the vein. The PIVC may then be used for fluid infusion and/or blood withdrawal or collection.

Oftentimes the PIVC assembly may include an extension tube, which may be used to infuse fluid and/or withdraw blood at a site removed from an insertion site of the catheter. This may reduce a risk of disturbing the insertion site or dislodging the catheter from the vasculature of the patient.

In some instances, a three-way stop valve may be coupled to the extension tube. The three-way stop valve may facilitate infusion via multiple medical devices coupled to different ports of the three-way stop valve. The three-way stop valve is often prone to growth of microorganisms due to the internal structure of the three-way stop valve and stagnate fluid within the three-way stop valve. The three-way stop valve or the extension tube may be secured to the patient, which may result in a bend in the extension tube and an increased likelihood of a kink in the extension tube. The kink may limit or prevent fluid flow through the catheter, inhibiting fluid infusion and blood withdrawal and endangering the patient.

The subject matter claimed herein is not limited to embodiments that solve any disadvantages or that operate only in environments such as those described above. Rather, this background is only provided to illustrate one example technology area where some implementations described herein may be practiced.

SUMMARY OF THE INVENTION

The present disclosure relates generally to intravenous catheter extension sets. In some embodiments, a vascular access system may include a catheter adapter and an extension set. In some embodiments, a catheter may extend distally from the catheter adapter. In some embodiments, the catheter may include a PIVC, a midline catheter, or a peripherally inserted central catheter ("PICC").

In some embodiments, the extension set may include one or more of the following: a first end, a second end, an extension tube between the first end and the second end, and a brace. In some embodiments, the first end may include a first connector and/or the second end may include a second connector. In some embodiments, the first connector may be configured to couple to the catheter adapter. In some embodiments, the brace may be configured to hold the extension tube in a curved position, which may reduce a likelihood of kinking of the extension tube and dislodging the catheter from an insertion site.

In some embodiments, the brace may include a hub, which may include an arm. In some embodiments, the arm may include a coupling portion configured to couple to the extension tube. In some embodiments, the extension tube may be curved between the hub and the coupling portion.

In some embodiments, the arm of the brace may be rigid. In some embodiments, the coupling portion of the arm may include an opening, and the extension tube may pass through the opening. In some embodiments, the coupling portion of the arm may include a snap feature configured to hold the extension tube.

In some embodiments, the extension set may include one or more other extension tubes, which may extend distally from the hub. In some embodiments, the other extension tubes may each include a distal end and a proximal end. In some embodiments, the second connector may be coupled to the distal end of a particular extension tube of the other extension tubes. In some embodiments, the second connector of the extension set may include one or more ports.

In some embodiments, the vascular access system may further include one or more needleless connectors, which may be coupled to the second connector. In some embodiments, the first connector and/or the second connector may include a luer lock. In some embodiments, the first connector and/or the second connector may include a check valve.

In some embodiments, the vascular access system may include a housing, which may be disposed between the first connector and the extension tube. In some embodiments, the housing may reduce a likelihood of kinking of the extension tube and dislodging the catheter from an insertion site. In some embodiments, the housing may be U-shaped or V-shaped and a fluid pathway may extend through the housing. In some embodiments, the housing may include a first end, a second end, and a fluid pathway extending through the first end and the second end. In some embodiments, the first end of the housing may be coupled to the first connector.

In some embodiments, the distal end of the extension tube may be coupled to the second end of the housing. In some embodiments, the fluid pathway of the housing may be in fluid communication with a fluid pathway of the extension tube.

In some embodiments, the extension set may include one or more additional extension tubes, which may extend distally from the second end of the housing. In some embodiments, each of the additional extension tubes may include a distal end and a proximal end. In some embodiments, the second connector may be coupled to the distal end of one or more of the additional extension tubes.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
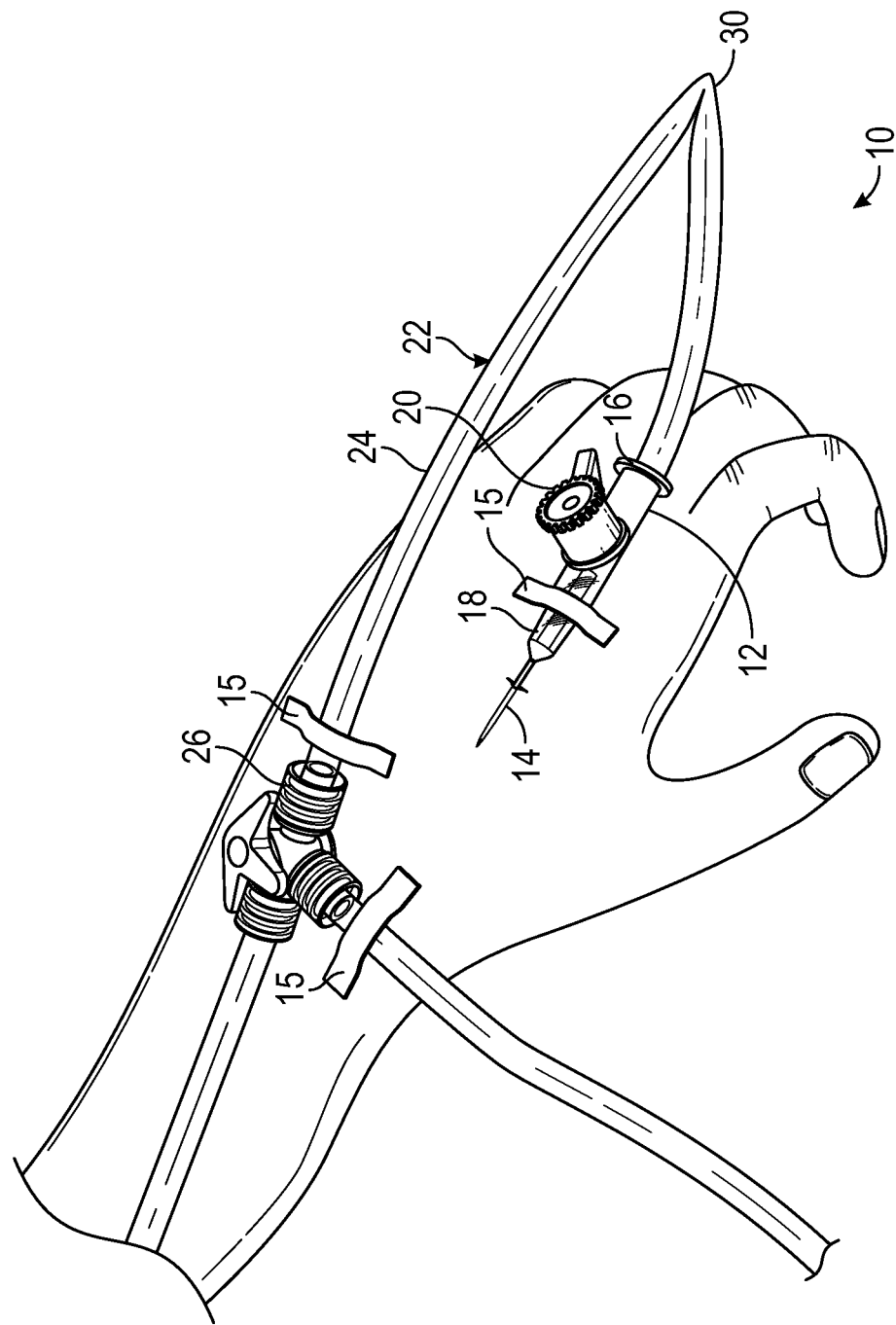
FIG. 1 is an upper perspective view of a prior art vascular access system, illustrating a kinked extension tube, according to some embodiments.
Figure 2A:
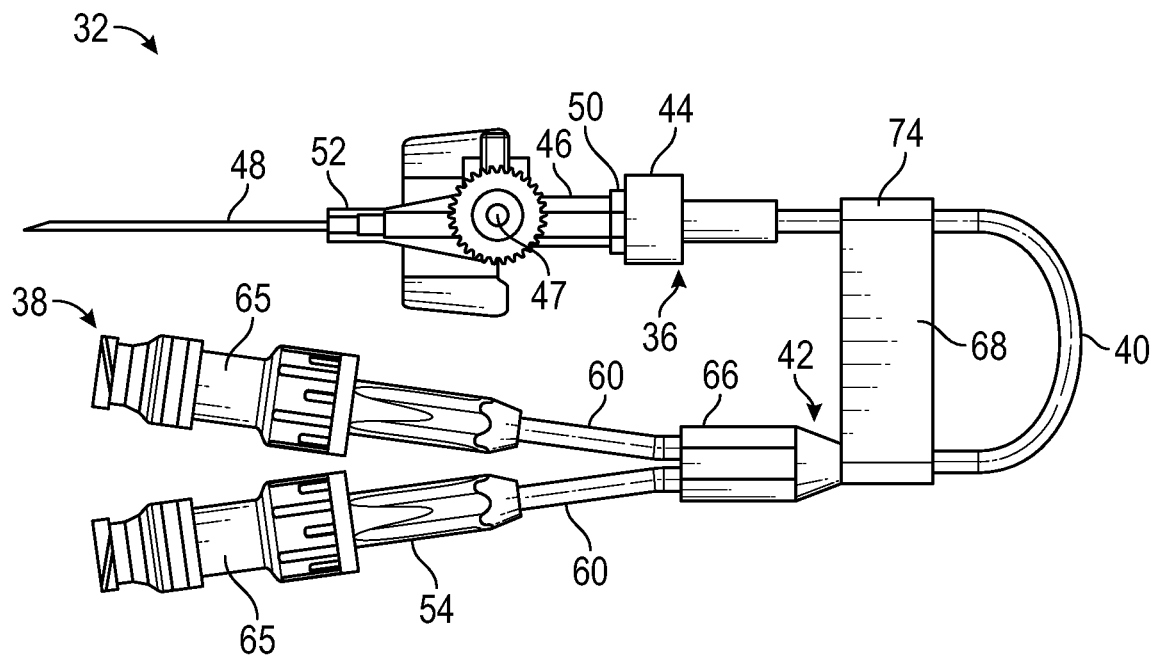
FIG. 2A is an upper perspective view of an example vascular access system, according to some embodiments.
Figure 2B:
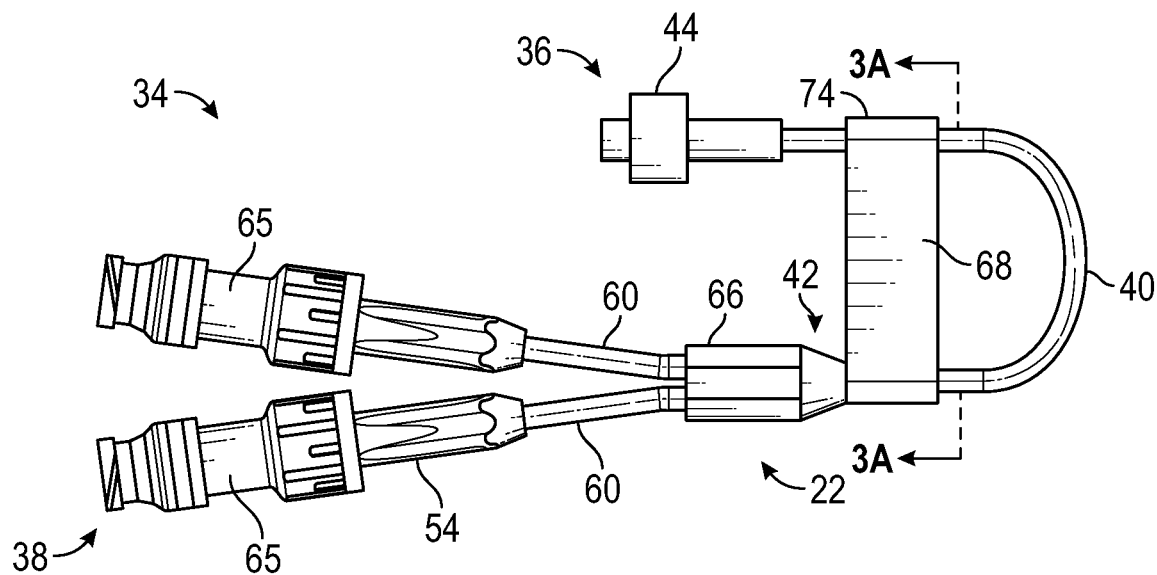
FIG. 2B is an upper perspective view of an example extension set of the vascular access system of FIG. 2A, according to some embodiments.
Figure 2C:
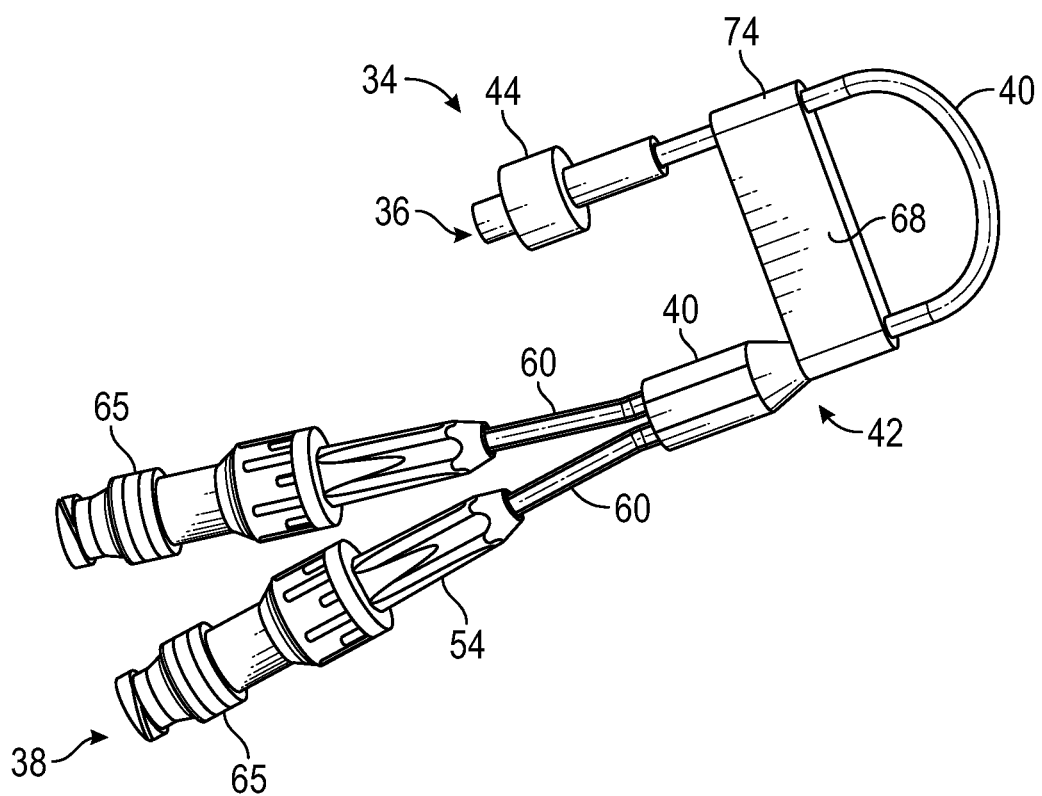
FIG. 2C is a lower perspective view of the extension set of FIG. 2B, according to some embodiments.
Figure 2D:
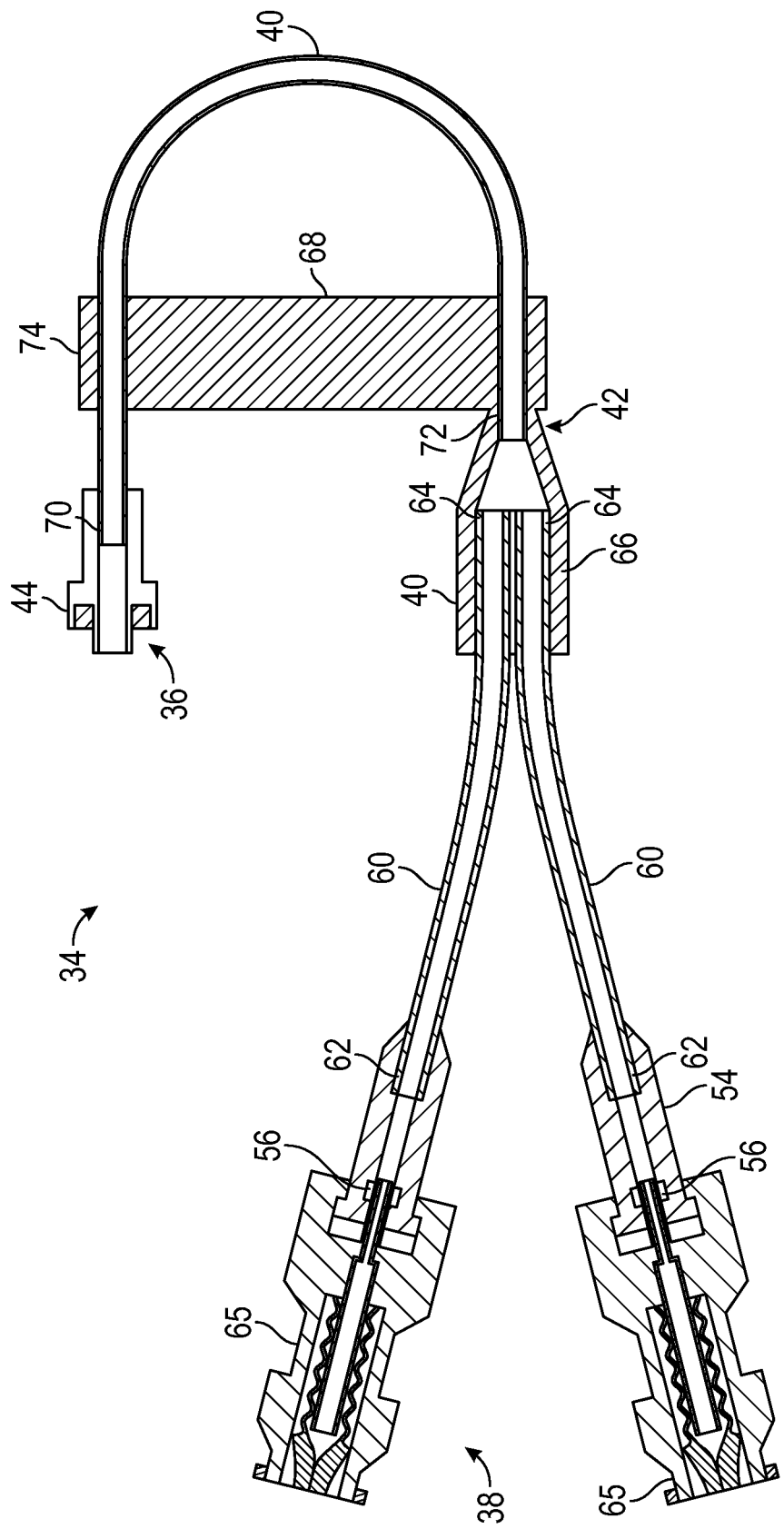
FIG. 2D is a cross-sectional view of the extension set of FIG. 2B, according to some embodiments.

The present disclosure relates generally to intravenous catheter extension sets. Referring now to FIG. 1, a prior art vascular access system 10 is illustrated. The prior art vascular access system 10 includes a catheter adapter 12 and a catheter 14 extending distally from the catheter adapter 12. The catheter adapter 12 includes a proximal end 16, a distal end 18, and a lumen extending therebetween. The catheter adapter 12 includes an injection port 20 in fluid communication with the lumen of the catheter adapter 12. To ensure that the catheter 14 remains in proper position, adhesive tape 15 is applied to the catheter adapter 12 to secure the catheter 14 within an insertion site where the catheter 14 is inserted through skin and into vasculature of a patient.

The prior art vascular access system 10 includes an extension set 22 coupled to the proximal end 16 of the catheter adapter 12. The extension set 22 includes an extension tube 24 that is coupled to a three-way valve 26. The three-way valve 26 enables more than one infusion device to be in fluid communication with the prior art vascular access system 10. The three-way valve 26 may be secured to the patient with adhesive tape 15. If the catheter adapter 12 and/or the three-way valve 26 are not adequately or appropriately secured with the adhesive tape 15, a kink 30 may form in the extension tube 24. The kink 30 may limit or prevent fluid flow through the catheter 14.

Referring now to FIG. 2A-2D, in some embodiments, a vascular access system 32 may include an extension set 34 and a catheter assembly. In some embodiments, the extension set 34 may include one or more of the following: a first end 36, a second end 38, an extension tube 40 between the first end 36 and the second end 38, and a brace 42. In some embodiments, the first end 36 may include a first connector 44, which may be coupled to a catheter adapter 46 of the catheter assembly. In some embodiments, the brace 42 may be configured to hold the extension tube 40 in a curved position. Thus, in some embodiments, the brace 42 may reduce a likelihood of kinking of the extension tube 40. In some embodiments, the brace 42 may also reduce a risk of dislodging a catheter 48 from the insertion site.

In some embodiments, the extension set 34 may be used with any suitable catheter assembly. In some embodiments, the catheter assembly may include the BD VENFLON™ Pro Safety Shielded IV Catheter. In these and other embodiments, the catheter adapter 46 may include an injection port 47 in fluid communication with a lumen of the catheter adapter 46.

In some embodiments, the catheter assembly may include the catheter adapter 46 and the catheter 48 extending distally from the catheter adapter 46. In some embodiments, the catheter 48 may include a peripheral IV catheter ("PIVC"), a midline catheter, or a peripherally inserted central catheter ("PICC"). In some embodiments, the catheter adapter 46 may include a proximal end 50, a distal end 52, and the lumen extending therebetween.

In some embodiments, the second end 38 of the extension set 34 may include a second connector 54, which may be configured to couple to a medical device, such as, for example, an infusion or blood withdrawal device. In some embodiments, the first connector 44 and/or the second connector 54 may include a male or female luer connector or another suitable connector. In some embodiments, the first connector 44 and/or the second connector 54 may include a luer-slip or luer-lock feature. In some embodiments, the first connector 44 may couple the extension set 34 to the proximal end 50 of the catheter adapter 46. In some embodiments, the extension set 34 may be removably coupled to the catheter adapter 46 via the first connector 44.

In some embodiments the first connector 44 and/or the second connector 54 may include a valve to prevent fluid from leaking out of the corresponding connector. In some embodiments, the valve 56 may include a one-way valve, a check valve, or another suitable valve.

In some embodiments, the extension set 34 may include one or more other extension tubes 60. In some embodiments, the other extension tubes 60 may each include a distal end 62 and a proximal end 64. In some embodiments, the second connector 54 may be coupled to the distal end 62 of a particular one of the other extension tubes 60.

In some embodiments, the second connector 54 may include one or more ports. In some embodiments, the second connector 54 may be configured to couple to a needleless connector 65. In some embodiments, one or more of the other extension tubes 60 may be coupled to a connector the same as or different from the second connector 54, which may facilitate coupling of the extension set 34 to various medical devices.

In some embodiments, the brace 42 may include a hub 66, which may include an arm 68 extending outwardly from a body of the hub 66. In some embodiments, an exterior of the hub 66 may include one or more surface features to improve gripping the hub 66 and the extension set 34. For example, the exterior of the hub 66 may include one or more protrusions. Additionally or alternatively, the exterior of the hub 66 may include one or more grooves. In some embodiments, the arm 68 may be monolithically formed as a single unit with a remaining portion of the hub 66.

In some embodiments, the other extension tubes 60 may extend from the hub 66. In some embodiments, the proximal ends 64 of the other extension tubes 60 may be coupled to the hub 66. For example, the proximal ends 64 of the other extension tubes 60 may be integrated with the hub 66. In some embodiments, the proximal ends 64 of the other extension tubes 60 may be removably coupled to the hub 66 via one or more connectors (not illustrated).

In some embodiments, the extension tube 40 may be coupled to the hub 66. In some embodiments, the extension tube 40 may include a first end 70 and a second end 72. In some embodiments, the second end 72 of the extension tube 40 may be coupled to the hub 66. For example, the second end 72 of the extension tube 40 may be integrated with the hub 66. In some embodiments, the second end 72 of the extension tube 40 may be removably coupled to the hub 66 via one or more connectors (not illustrated).

In some embodiments, the extension tube 40 may be elongated and extend through the hub 66 and couple directly to the second connector 54. In some embodiments, the hub 66 may include the second connector 54 and the extension tube 40 may terminate within the hub 66. In these and other embodiments, the vascular access system 32 may not include the other extension tubes 60.

In some embodiments, the hub 66 may include a lumen extending therethrough such that the second end 72 of the extension tube 40 may be in fluid communication with the other extension tubes 60. In some embodiments, a fluid pathway extending through the extension set 34 may include one or more of the following: the first connector 44, the extension tube 40, the hub 66, the other extension tubes 60, and the second connector 54.

In some embodiments, the arm 68 may include a coupling portion 74 configured to couple to the extension tube 40. In some embodiments, the extension tube 40 may be curved between the hub 66 and the coupling portion 74. In some embodiments, the extension tube 40 may be integrated with the coupling portion 74 or removably coupled with the coupling portion 74.

In some embodiments, the brace 42 may be constructed of a rigid material. In some embodiments, the brace 42 may be constructed of plastic, such as, for example, polyethylene. In some embodiments, the brace 42 may be constructed from any suitable material including, for example, nylon, vinyl, polyurethane, etc. In some embodiments, the hub 66 may be constructed of a more rigid material than the arm 68. In some embodiments, the second end 72 of the extension tube 40 may be aligned with a longitudinal axis of the hub 66.

Figure 3A:
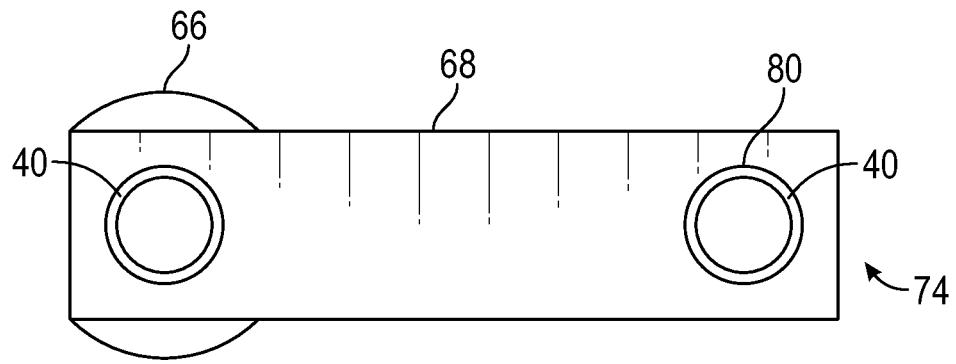
FIG. 3A is a proximal end view of an example brace along the line 3A-3A of FIG. 2B, according to some embodiments.

Referring now to FIG. 3A, in some embodiments, the coupling portion 74 may include an enclosed opening 80 that extends through the arm 68, and the extension tube 40 may extend through the enclosed opening 80.

Figure 3B:
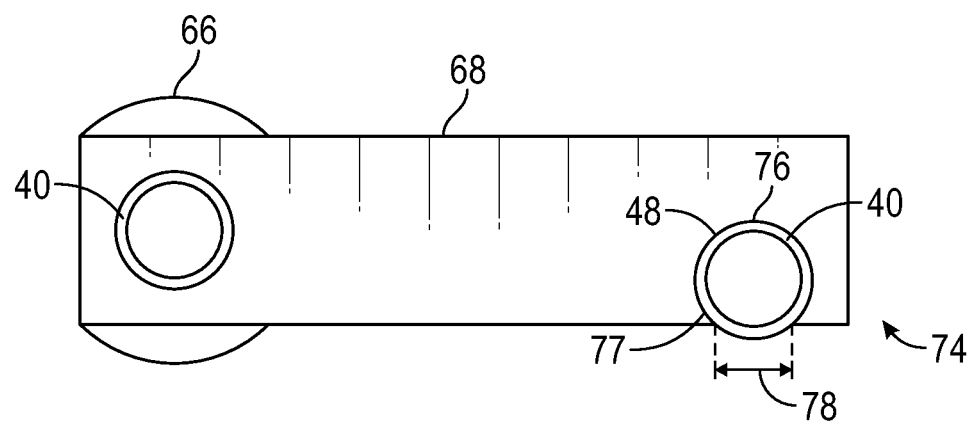
FIG. 3B is a proximal end view of another example brace, according to some embodiments.

Referring now to FIG. 3B, the coupling portion 74 may include a snap mechanism 76 or a fastener, which may couple the extension tube 40 to the arm 68. In some embodiments, the snap mechanism 76 and/or the fastener may facilitate removable coupling of the extension tube 40 to the arm 68. In some embodiments, the snap mechanism 76 may include an opening 77, which may include a diameter 78 less than an outer diameter of the extension tube 40 such that the extension tube 40 snaps within the opening 77. In some embodiments, the fastener (not illustrated) may include a clip, clasp, hook, strap, or other suitable fastener.

Figure 4A:
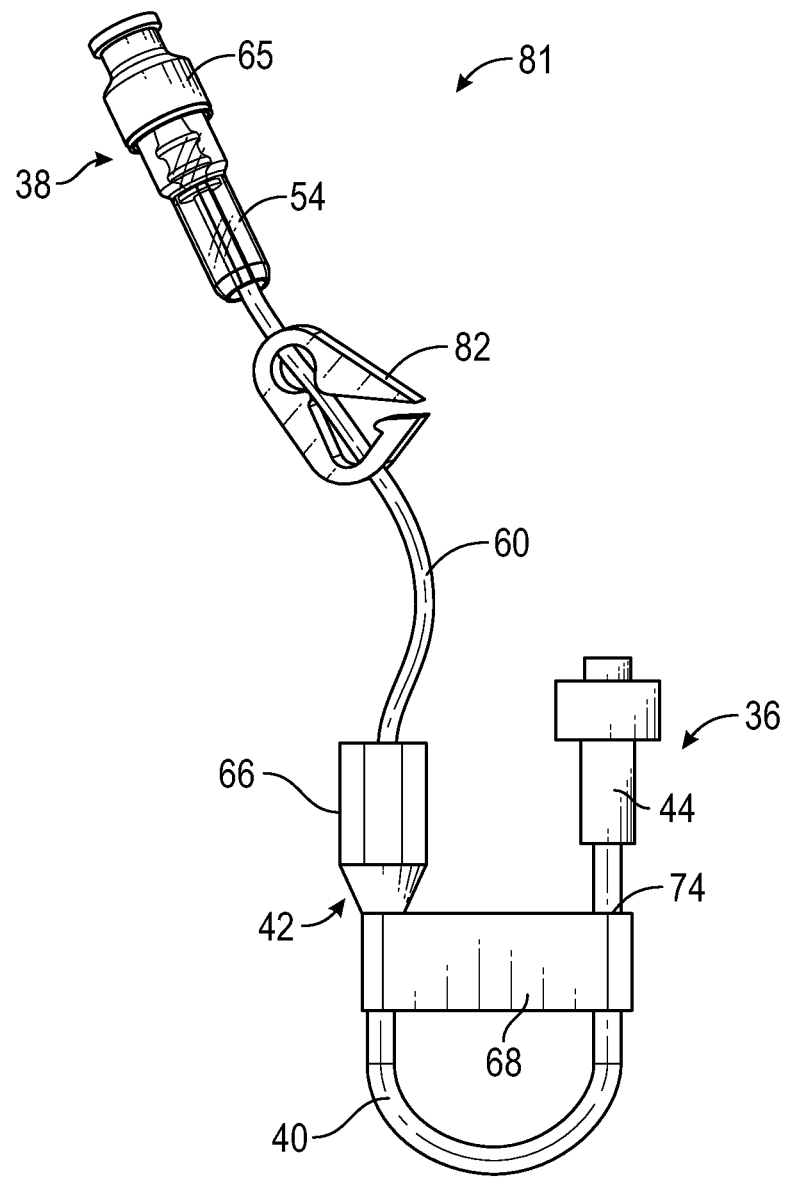
FIG. 4A is an upper perspective view of another example extension set, according to some embodiments.

Referring now to FIG. 4A, an extension set 81 is illustrated, according to some embodiments. In some embodiments, the extension set 81 may include or correspond to the extension set 34 described with respect to FIGS. 2-3. In some embodiments, the extension set 81 may include only one of the other extension tubes 60.

In some embodiments, the other extension tube 60 may include a clamp 82. In some embodiments, the clamp 82 may selectively close off the other extension tube 60 to prevent fluid from flowing through the other extension tube 60. It is understood that in some embodiments, one or more of the other extension tubes 60 described with respect to FIG. 2 may include the clamp 82.

Figure 4B:
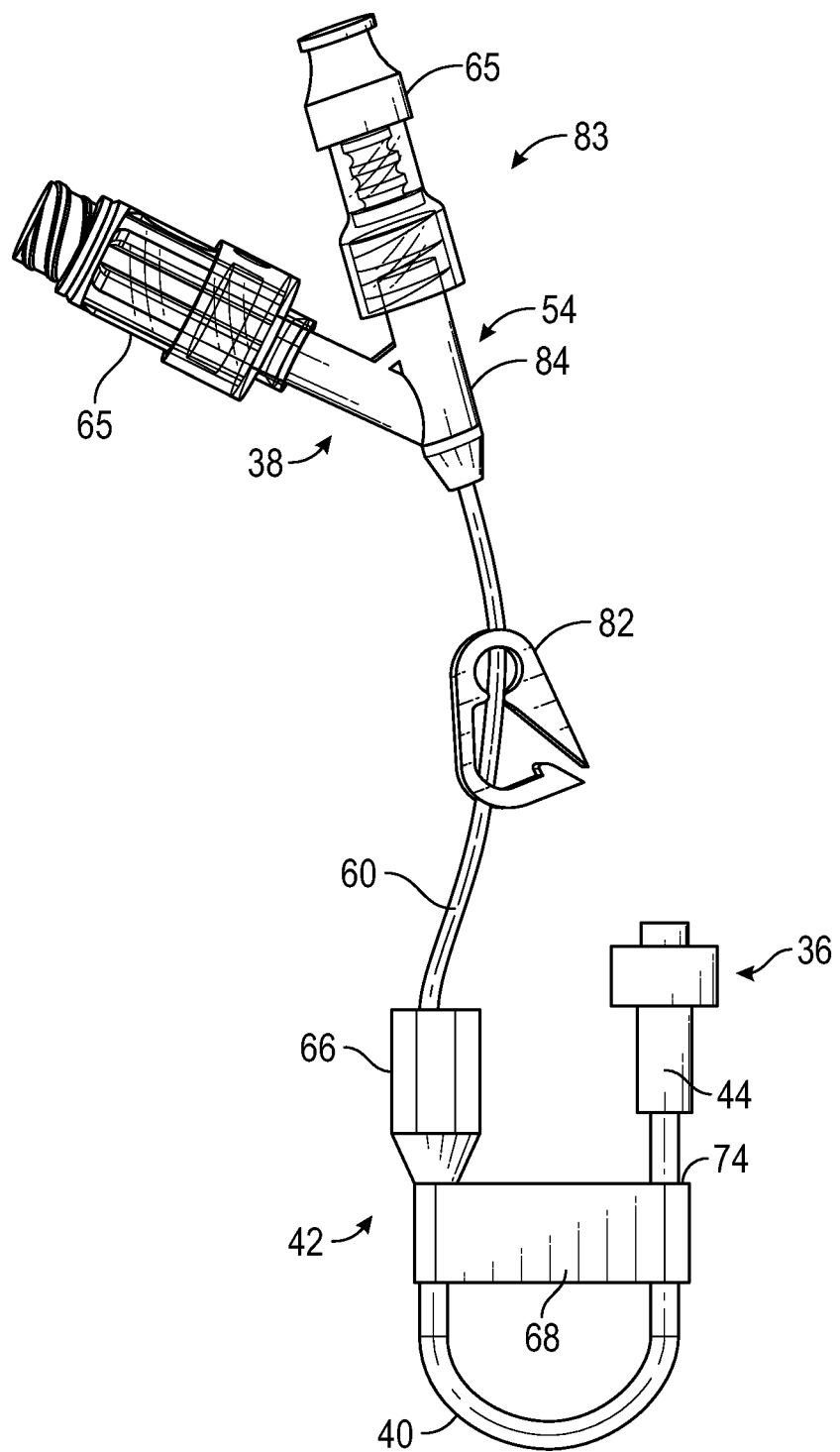
FIG. 4B is an upper perspective view of another example extension set, according to some embodiments.

Referring now to FIG. 4B, an extension set 83 is in some embodiments, the second connector 54 may include a Y-adapter 84 or another suitable connector. In some embodiments, a needleless connector 65 may be coupled to the Y-adapter 84. In some embodiments, the second connector 54 of the extension set 34 and/or the extension set 81 may include the Y-adapter 84.

Figure 5A:
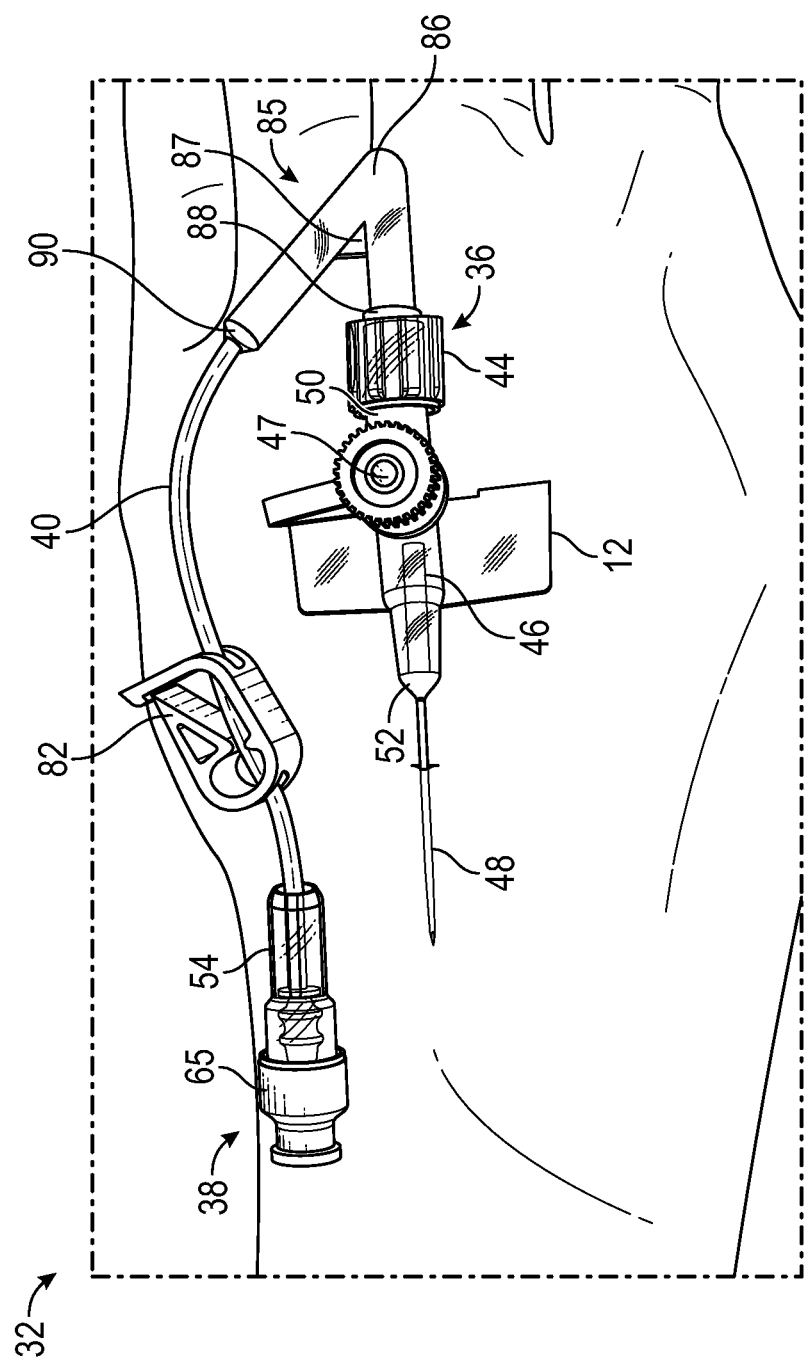
FIG. 5A is an upper perspective view of the vascular access system of FIG. 2A, according to some embodiments.
Figure 5B:
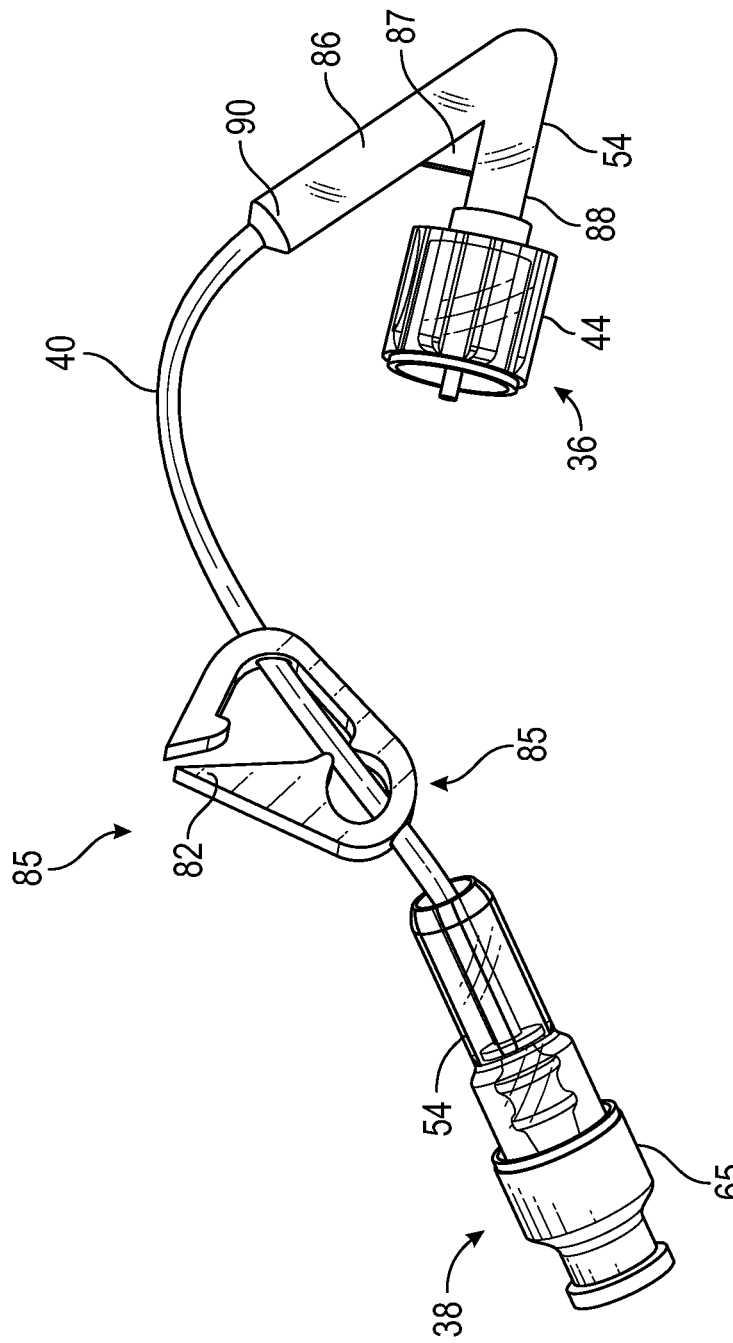
FIG. 5B is an upper perspective view of another example extension set, according to some embodiments.
Figure 5C:
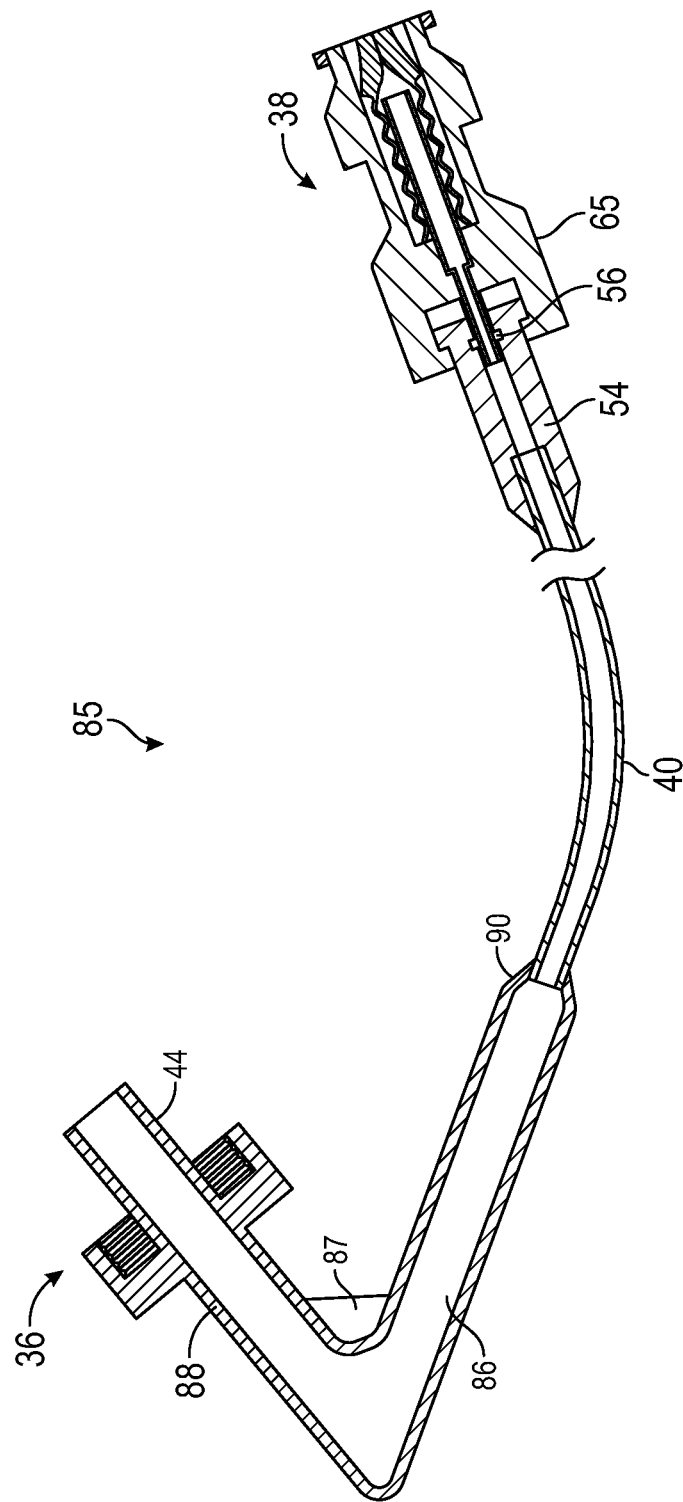
FIG. 5C is a cross-sectional view of the extension set of FIG. 5B, according to some embodiments.

Referring now to FIGS. 5A-5C, in some embodiments, the vascular access system 32 may include an extension set 85. In some embodiments, the extension set 85 may include or correspond to one or more of the extension set 34 described with respect to FIGS. 2-3, the extension set 81 described with respect to FIG. 4A, and the extension set 81 described with respect to FIG. 4B.

In some embodiments, the first end 36 of the extension set 85 may include the first connector 44, which may be coupled to the catheter adapter 46. In some embodiments, the second end 38 may include the second connector 54. In some embodiments, the extension tube 40 may be disposed between the first end 36 and the second end 38. In some embodiments, the extension set 85 may include a housing 86, which may be disposed between the first connector 44 and the extension tube 40. In some embodiments, the housing 86 may reduce a risk of kinking the extension tube 40 compared to if the extension tube 40 was coupled directly to the first connector 44.

In some embodiments, the housing 86 may include a first end 88 and a second end 90. In some embodiments, the first end 88 may be coupled to the first connector 44. In some embodiments, the housing 86 may be monolithically formed as a single unit with the first connector 44. In some embodiments, the first connector 44 may include a male or female luer connector or another suitable connector. In some embodiments, the first connector 44 may include a luer-slip or luer-lock feature. As mentioned, in some embodiments, the first connector 44 may include the valve 56 to prevent fluid from leaking out of the first connector 44. In some embodiments, the valve 56 may include a one-way valve, a check valve, or another suitable valve.

In some embodiments, the second end 90 may be coupled to the extension tube 40. In some embodiments, the housing 86 may be generally U-shaped or generally V-shaped. In some embodiments, a fluid pathway 92 may extend through the housing 86.

In some embodiments, the housing 86 may be constructed of plastic, such as, for example, polyethylene or another suitable plastic. In some embodiments, the housing 86 may be constructed of a rigid material. In some embodiments, the housing 86 may be constructed from any suitable material including, for example, nylon, vinyl, polyurethane, etc. In some embodiments, portions of the housing 86 may be constructed of flexible material or plastic and other portions may be constructed of a more rigid material.

In some embodiments, the housing 86 may be transparent or translucent. In some embodiments, the housing 86 may further include a support 87 extending between two arms forming a U-shape or a V-shape of the housing 86. In some embodiments, the support 87 may help retain the U-shape or the V-shape of the housing 86. In some embodiments, the housing 86 may not include the support 87.

In some embodiments, the distal end 62 of the extension tube 40 may be coupled to the second end 90 of the housing 86. In some embodiments, the proximal end 64 of the extension tube 40 may be coupled to the second connector 54. In some embodiments, the second connector 54 may be coupled to the needleless connector 65.

Figure 6A:
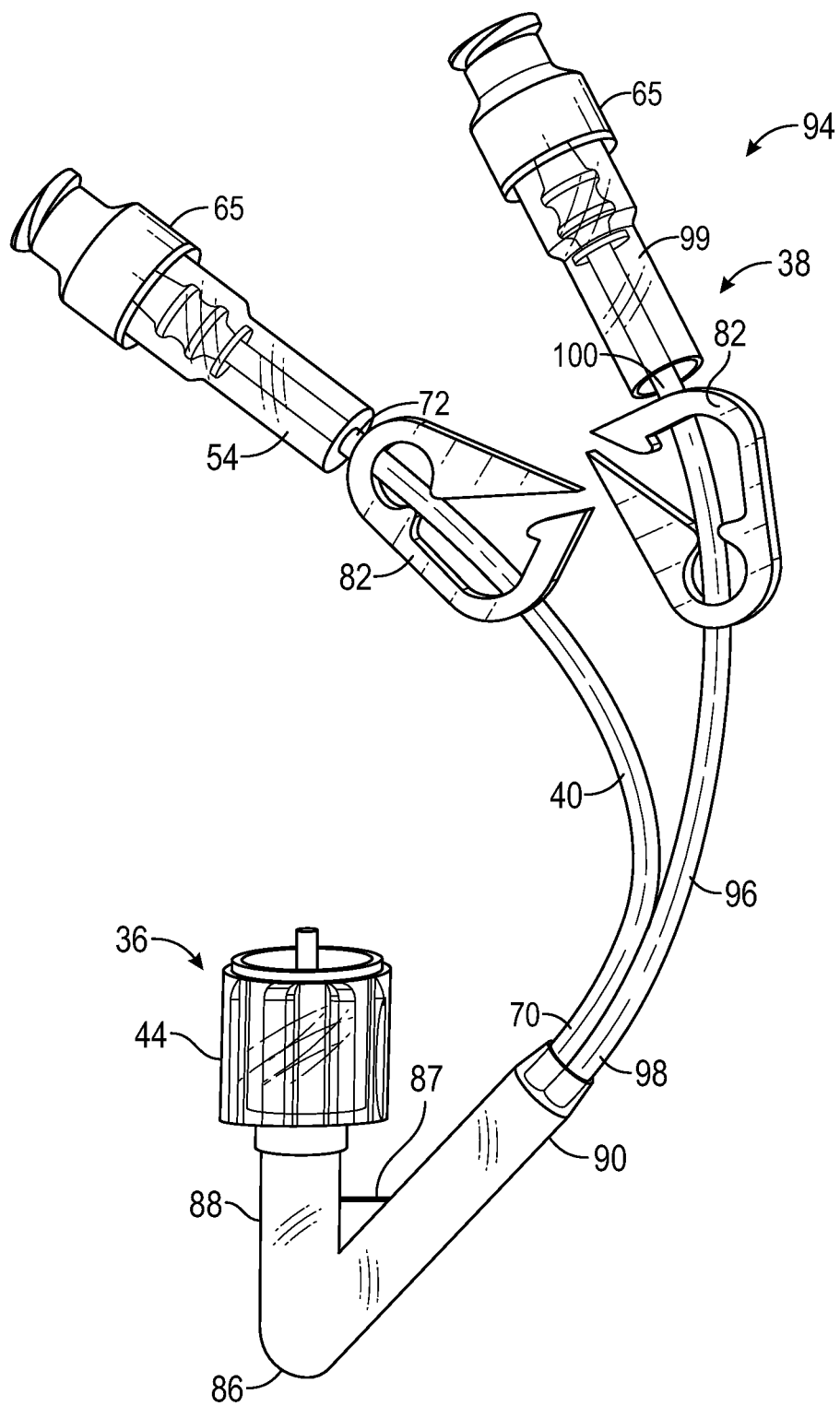
FIG. 6A is an upper perspective view of another example extension set, according to some embodiments.

Referring now to FIG. 6A, in some embodiments, an extension set 94 may include another extension tube 96, which may extend distally from the second end 90 of the housing 86. In some embodiments, the extension set 94 may include or correspond to one or more of the extension set 34 described with respect to FIGS. 2-3, the extension set 81 described with respect to FIG. 4A, the extension set 83 described with respect to FIG. 4B, and the extension set 85 described with respect to FIG. 5.

In some embodiments, the other extension tube 96 may include a distal end 98, which may be coupled to the second end 90 of the housing 86. For example, the distal end 98 may be integrated with the second end 90 of the housing 86, as illustrated, for example, in FIG. 6A. In some embodiments, the distal end 98 may be removably coupled to the second end 90 of the housing 86 via one or more connectors (not illustrated).

In some embodiments, the other extension tube 96 may include a proximal end 100, which may be coupled to another connector 99. In some embodiments, the other connector 99 may be the same as or different from the second connector 54.

Figure 6B:
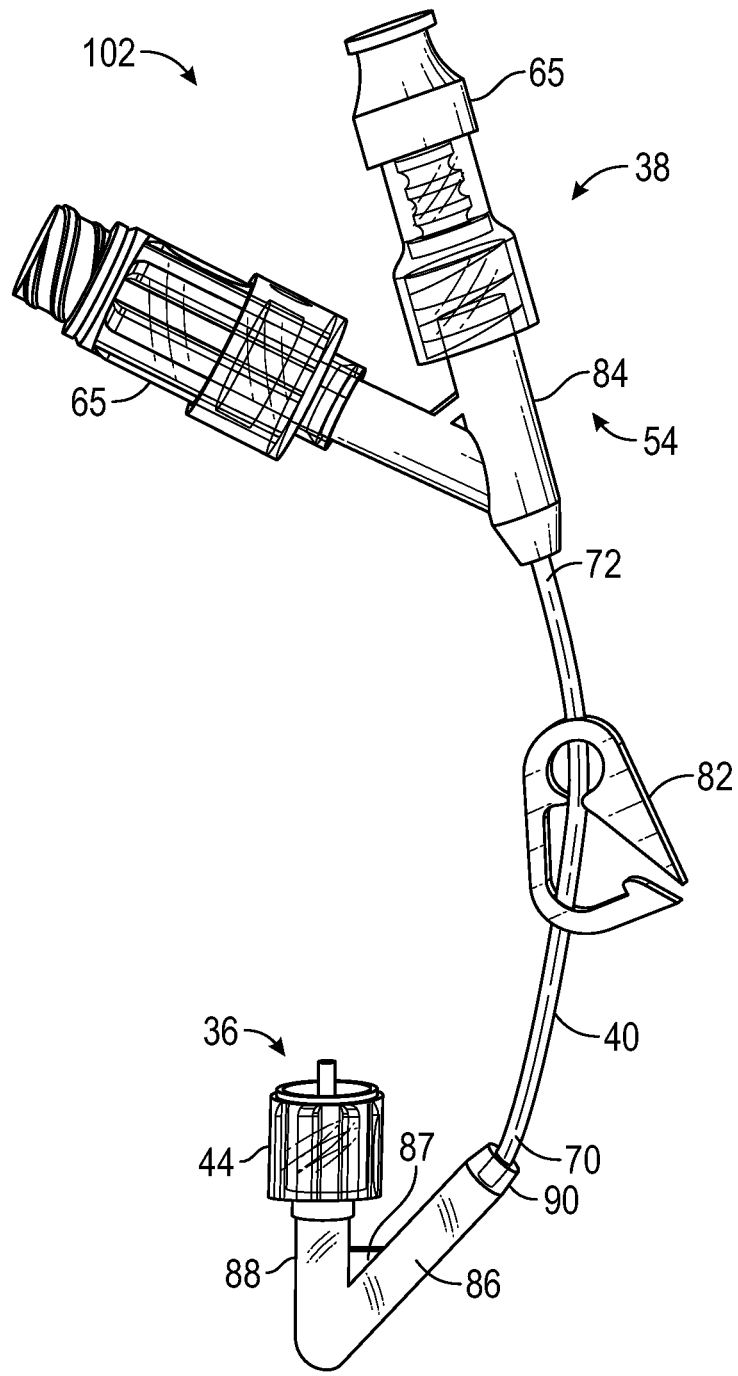
FIG. 6B is an upper perspective view of another example extension set, according to some embodiments.

Referring now to FIG. 6B, another extension set 102 may include the Y-adapter 84 or another suitable connector. In some embodiments, the needleless connector 65 may be coupled to the Y-adapter 84. In some embodiments, the second connector 54 of the extension set 83 and/or the extension set 94 may include the Y-adapter 84. In some embodiments, the extension tube 40 and/or the other extension tube 96 may include the clamp 82.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. An extension set, comprising:
   a first connector comprising a luer lock connector;
   a housing, comprising a first end, a second end, and a fluid pathway extending through the first end and the second end, wherein the first end is coupled to the first connector, wherein the housing comprises a V-shape or a U-shape between the first end and the second end, wherein the V-shape or the U-shape is closed between the first end and the second end, wherein the luer lock connector is monolithically formed as a single unit with the V-shape or the U-shape;
   an extension tube comprising a distal end and a proximal end, wherein the distal end is coupled to the second end of the housing, wherein the fluid pathway of the housing is in fluid communication with a fluid pathway of the extension tube; and
   a second connector coupled to the proximal end of the extension tube.

2. The extension set of claim 1, wherein the extension set further comprises another extension tube extending distally from the second end of the housing, wherein the another extension tube comprises a distal end and a proximal end, wherein a third connector is coupled to the distal end of the another extension tube.

3. The extension set of claim 1, further comprising a needleless connector coupled to the second connector.

4. The extension set of claim 1, wherein the first connector comprises the luer lock connector, wherein the luer lock connector comprises a check valve.

5. The extension set of claim 1, wherein the housing is monolithically formed as a single unit with the first connector.

6. An extension set, comprising:
   a first end comprising a first connector configured to couple to a catheter adapter;
   a second end comprising a second connector;
   a first extension tube disposed between the first end and the second end; and
   a brace configured to hold the first extension tube in a curved position, wherein the brace comprises a rigid arm and a hub extending directly from the rigid arm, wherein the hub is perpendicular to a longitudinal axis of the rigid arm, wherein the rigid arm comprises a coupling portion configured to couple to the first extension tube, wherein the first extension tube is curved between the hub and the coupling portion, wherein the hub is distal to the coupling portion;
   a second extension tube extending directly from the hub and in fluid communication with the first extension tube; and
   a third extension tube extending directly from the hub and in fluid communication with the first extension tube.

7. The extension set of claim 6, wherein the coupling portion of the rigid arm comprises an enclosed opening, wherein the first extension tube extends through the enclosed opening.

8. The extension set of claim 6, wherein the coupling portion of the rigid arm comprises a snap feature configured to hold the first extension tube.

9. The extension set of claim 6, wherein the second extension tube comprises a distal end and a proximal end, wherein the second connector is coupled to the distal end of the second extension tube.

10. The extension set of claim 6, further comprising a needleless connector coupled to the second connector.

11. The extension set of claim 6, wherein the first connector comprises a luer lock connector, wherein the luer lock connector comprises a check valve.

12. The extension set of claim 6, wherein the second connector comprises a multi-port connector.

* * * * *